(12) United States Patent
Yuan et al.

(10) Patent No.: US 11,963,788 B2
(45) Date of Patent: Apr. 23, 2024

(54) GRAPH-BASED PROSTATE DIAGNOSIS NETWORK AND METHOD FOR USING THE SAME

(71) Applicant: City University of Hong Kong, Hong Kong (HK)

(72) Inventors: Yixuan Yuan, Hong Kong (HK); Zhen Chen, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 370 days.

(21) Appl. No.: 17/553,812

(22) Filed: Dec. 17, 2021

(65) Prior Publication Data
US 2023/0190179 A1 Jun. 22, 2023

(51) Int. Cl.
*A61B 5/00* (2006.01)
*A61B 5/055* (2006.01)
(Continued)

(52) U.S. Cl.
CPC ............ *A61B 5/4381* (2013.01); *A61B 5/004* (2013.01); *A61B 5/055* (2013.01); *A61B 5/7267* (2013.01);
(Continued)

(58) Field of Classification Search
CPC ....... A61B 5/4381; A61B 5/004; A61B 5/005; A61B 5/7267; A61B 5/7275; G16H 30/20; G16H 50/20; G01R 33/5608
(Continued)

(56) References Cited

U.S. PATENT DOCUMENTS

| 9,779,213 B2 | 10/2017 | Donovan et al. |
|---|---|---|
| 10,018,712 B2 | 7/2018 | Moradi et al. |

(Continued)

FOREIGN PATENT DOCUMENTS

| CN | 107133638 A | 9/2017 |
|---|---|---|
| CN | 111028206 A | 4/2020 |
| WO | 2018156778 A1 | 8/2018 |

OTHER PUBLICATIONS

Geert Litjens, Oscar Debats, Jelle Barentsz, Nico Karssemeijer, and Henkjan Huisman. "ProstateX Challenge data", The Cancer Imaging Archive (2017). DOI: 10.7937/K9TCIA.2017.MURS5CL.
(Continued)

*Primary Examiner* — Michael R Neff
(74) *Attorney, Agent, or Firm* — Idea Intellectual Limited; Margaret A. Burke; Sam T. Yip

(57) ABSTRACT

The present invention provides a graph-based prostate diagnosis network (GPD-Net) and a method for using the same to predict a prostate health status of a patient from a 3D magnetic resonance imaging (MRI) scan containing a plurality of 2D MRI slices. The GPD-Net only demands patient-level annotations of MRI scan for training by formulating the diagnosis task of 3D prostate MRI scan in a multi-instance learning (MIL) strategy, and regarding each 2D MRI slice in the 3D prostate MRI scan as an instance. The GPD-Net includes a plurality of importance-guided graph convolutional layers to explore the diagnostic information with the importance-based topology. The present invention provides accurate prediction of prostate diseases and achieve more reliable diagnosis from MRI scans, therefore can effectively alleviate the workload of clinician in viewing the slices of MRI scan.

18 Claims, 5 Drawing Sheets

(51) Int. Cl.
  *G01R 33/56* (2006.01)
  *G16H 30/20* (2018.01)
  *G16H 50/20* (2018.01)

(52) U.S. Cl.
  CPC ........ *A61B 5/7275* (2013.01); *G01R 33/5608* (2013.01); *G16H 30/20* (2018.01); *G16H 50/20* (2018.01)

(58) Field of Classification Search
  USPC ........................................................ 382/128
  See application file for complete search history.

(56) References Cited

U.S. PATENT DOCUMENTS

| | | |
|---|---|---|
| 2019/0156477 A1 | 5/2019 | Perrin et al. |
| 2020/0167930 A1* | 5/2020 | Wang ........................ G06N 3/08 |
| 2022/0122250 A1* | 4/2022 | Besson ................. G06T 7/0012 |
| 2022/0208355 A1* | 6/2022 | Li ............................ G06T 7/174 |

OTHER PUBLICATIONS

Armato S G, Huisman H, Drukker K, et al. PROSTATEx Challenges for computerized classification of prostate lesions from multiparametric magnetic resonance images[J]. Journal of Medical Imaging, 2018, 5(4): 044501-1~9.

\* cited by examiner

US 11,963,788 B2

GRAPH-BASED PROSTATE DIAGNOSIS NETWORK AND METHOD FOR USING THE SAME

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION:

The present invention generally relates to machine learning prostate diagnosis, more specifically, a graph-based prostate diagnosis network for prostate diagnosis on magnetic resonance imaging (MRI) scans.

BACKGROUND OF THE INVENTION

Prostate cancer is the second most common type of cancer in men. In clinical practice, the screening of prostate cancer using prostate specific antigen (PSA) test and digital rectal examination (DRE) has very limited diagnostic accuracy and may lead to over-diagnosis. In order to screen patients with potential prostate disease in the early stage and avoid unnecessary biopsy, artificial intelligence (AI)-assisted or machine learning diagnostic algorithms can utilize MRI to provide the diagnostic prediction of prostate health status, including the existence of clinically significant biomarkers and the Gleason grading score. However, existing AI-assisted diagnostic algorithms require collection of a large amount of dataset with detailed manual annotations, which demands high cost of time and labor.

SUMMARY OF THE INVENTION

The present invention provides a graph-based prostate diagnosis network (GPD-Net) and a method for using the same which can provide accurate prediction of prostate diseases and achieve more reliable diagnosis from MRI scans, therefore can effectively alleviate the workload of clinician in viewing the slices of MRI scan.

According to one aspect of the present invention, a graph-based prostate diagnosis network (GPD-Net) for predicting a prostate health status of a patient from a 3D magnetic resonance imaging (MRI) scan containing a plurality of 2D MRI slices. The GPD-Net comprises: a feature extractor configured to extract a plurality of preliminary instance embeddings corresponding to the plurality 2D MRI slices respectively; a pooling operator configured to aggregate the plurality of preliminary instance embeddings together to generate a preliminary bag embedding; a preliminary classifier configured to calculate an instance importance parameter based on the preliminary bag embedding; an instance importance calculator configured to calculate a plurality of instance importances corresponding to the plurality of preliminary instance embeddings respectively based on the instance importance parameter; and a plurality of importance-guided graph (IGraph) layers configured to generate a plurality of improved instance embeddings by performing a plurality of graph convolutions on the plurality of preliminary instance embeddings in a sequential manner; an embedding aggregator configured to generate an improved bag embedding by aggregating the plurality of improved instance embeddings with the plurality of instance importances; and a refined classifier configured to process the improved bag embedding to generate a refined diagnosis prediction for predicting prostate health status of the patient.

According to another aspect of the present invention, a method using a graph-based prostate diagnosis network is provided to predict a prostate health status of a patient from a 3D magnetic resonance imaging (MRI) scan containing a plurality of 2D MRI slices. The method comprising: an instance embedding extraction stage including extracting, by a feature extractor, a plurality of preliminary instance embeddings corresponding to the plurality of 2D MRI slices respectively; a preliminary diagnosis stage including: aggregating, by a pooling operator, the plurality of preliminary instance embeddings together to generate a preliminary bag embedding; and calculating, by a preliminary classifier, an instance importance parameter based on the preliminary bag embedding; an instance importance calculation stage including calculating, by an instance importance calculator, a plurality of instance importances corresponding to the plurality of preliminary instance embeddings respectively based on the instance importance parameter; and a refined diagnosis stage including: generating, by a plurality of importance-guided graph (IGraph) layers, a plurality of improved instance embeddings by performing a plurality of graph convolutions on the plurality of preliminary instance embeddings in a sequential manner; generating, by an embedding aggregator, an improved bag embedding by aggregating the plurality of improved instance embeddings with the plurality of instance importances; and processing, by a refined classifier, the improved bag embedding to generate a refined diagnosis prediction y for predicting prostate health status of the patient.

Different from existing machine learning networks that require detailed manual annotations (e.g., the pixel-wise, patch-wise or slice-wise annotations) of 3D MRI scan for training, the present invention only demands patient-level annotations of MRI scan for training by formulating the diagnosis task of 3D prostate MRI scan in a multi-instance learning (MIL) strategy, and regarding each slice in 3D scan as the instance.

BRIEF DESCRIPTION OF THE DRAWINGS

Embodiments of the invention are described in more detail hereinafter with reference to the drawings, in which.

DETAILED DESCRIPTION

In the following description, exemplary embodiments of the present invention are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

Figure 1:
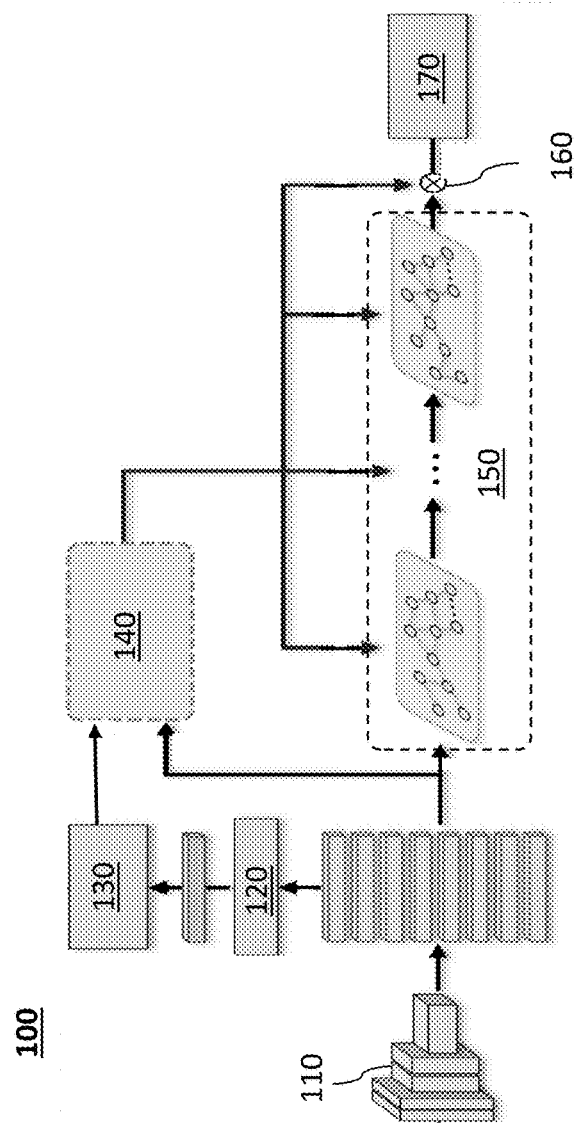
FIG. 1 shows a block diagram of a GPD-Net according to one embodiment of the present invention.

FIG. 1 shows a block diagram of a GPD-Net 100 according to one embodiment of the present invention. As shown, the GPD-Net 100 may comprise a feature extractor 110, a pooling operator 120, a preliminary classifier 130, an instance importance calculator 140, a plurality of importance-guided graph (IGraph) layers 150, an embedding aggregator 160 and a refined classifier 170.

The GPD-Net 100 may be configured and trained for doing a diagnosis task to predict prostate health status of a patient based on a 3D magnetic resonance imaging (MRI) scan from that patient. The diagnosis task may be formulated in a multi-instance learning (MIL) strategy in which each 2D MRI slice of the 3D MRI scan is regarded as an instance. The GPD-Net 100 only demands 3D MRI scans with patient-level annotations (or labels) for training. Therefore, the time and labor cost of collecting these patient-level labels is significantly reduced, compared with the detailed manual labels in existing methods.

The 3D MRI scans can be one or several modals of multiparametric MRI (mpMRI) scans, including but not limited to, diffusion weighted images (DWI), apparent diffusion coefficient (ADC) maps, Ktrans (a measure of capillary permeability obtained using dynamic contrast-enhanced (DCE) MR perfusion), and T2 weighted images (T2WI).

The diagnosis performance of the trained GPD-Net can be evaluated on specific dataset by collecting prostate MRI scans and corresponding patient-level labels. There are two publicly available datasets for the diagnostic assessment, including the PROSTATEx dataset for the prediction of existence of clinically significant lesion, and PROSTATEx-2 dataset for the prediction of Gleason score.

Figure 2:
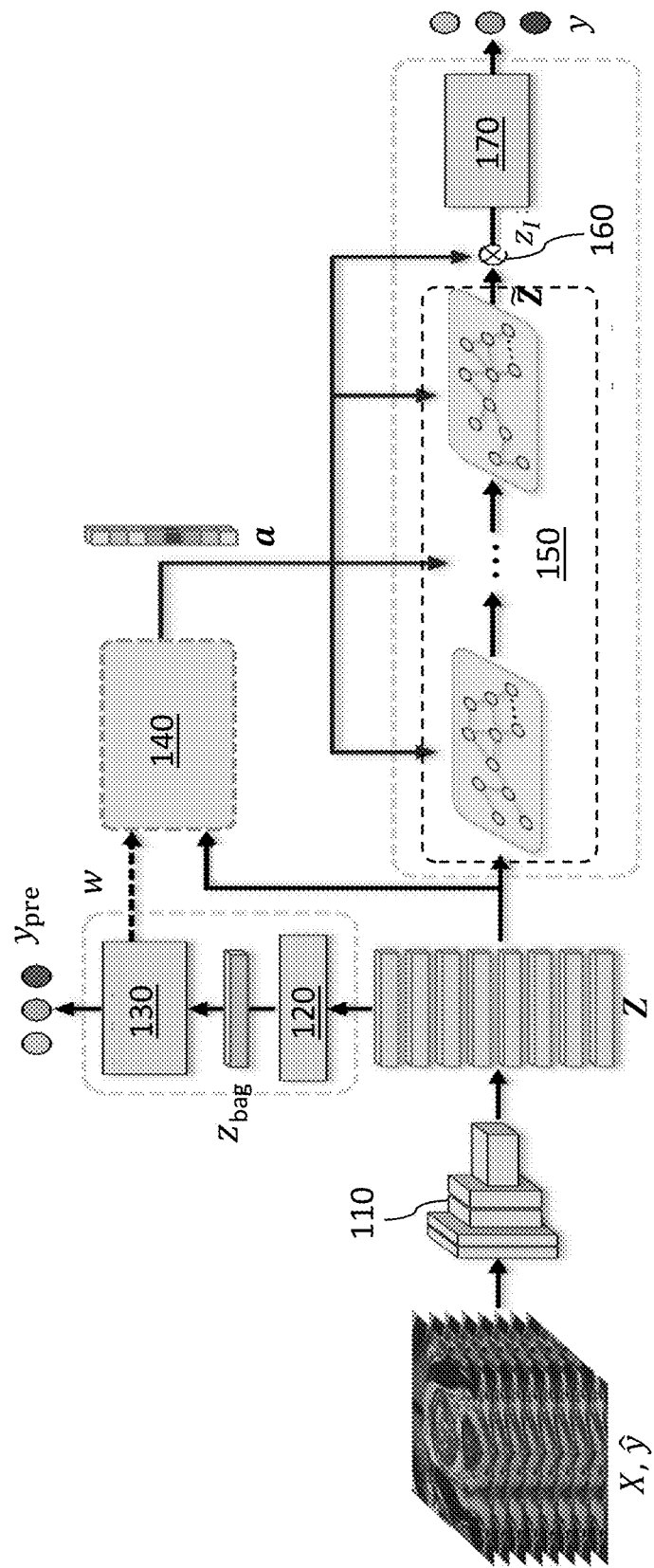
FIG. 2 shows an arrangement for training the GPD-Net to predict prostate health status of a patient according to one embodiment of the present invention.

FIG. 2 shows an arrangement for training the GPD-Net 100 to predict prostate health status of a patient. A training dataset of 3D MRI scans are prepared such that each 3D MRI scan has a patient-level label $\hat{y}$ indicating a prostate health status of a patient and contains K corresponding 2D MRI slices X (X={$x_k$}$_{k=1}^K$). By way of example, the patient-level label $\hat{y}$ can be an existence of clinically significant biomarkers or a Gleason grading score.

The feature extractor 110 is configured and trained for extracting, for each of the 3D MRI scans, K preliminary instance embeddings corresponding to the K 2D MRI slices respectively. The K preliminary instance embeddings are denoted as Z={$z_k$}$_{k=1}^K$, where $z_k$ is the preliminary instance embedding corresponding to the $k^{th}$ 2D MRI slice in the 3D MRI scan. Each preliminary instance embedding can be regarded as embedding feature of the corresponding 2D MRI slice and implemented as feature maps or feature vectors.

The feature extractor 110 can be implemented by any suitable type of 2D convolutional neural network (2D-CNN), such as a residual neural network (ResNet) or a visual geometry group (VGG) neural network. In other words, the instance embeddings can be achieved as feature maps or feature vectors of each 2D slice via the 2D CNN.

The pooling operator 120 is configured and trained for aggregating the preliminary instance embeddings Z together to generate a preliminary bag embedding $z_{bag}$.

The preliminary bag embedding $z_{bag}$ can be achieved with various algorithms. In one embodiment, the preliminary bag embedding may be achieved by summing up the preliminary instance embeddings. That is the preliminary bag embedding is given by $z_{bag}=\Sigma z_k$, for k=1, . . . , K. In one embodiment, the preliminary bag embedding may be achieved by averaging the preliminary instance embeddings. That is the preliminary bag embedding is given by $$z_{bag} = \frac{\sum z_k}{K},$$

for k=1, . . . , K. In one embodiment, the preliminary bag embedding may be achieved by finding the maximum of the preliminary instance embeddings. That is the preliminary bag embedding is given by $z_{bag}=\max(z_k)$, for k=1, . . . , K.

The preliminary classifier 130 is configured and trained for processing the preliminary bag embedding $z_{bag}$ to generate a preliminary diagnosis prediction $y_{pre}$, and calculating an instance importance parameter w.

The preliminary diagnosis prediction $y_{pre}$ may be supervised with a loss function measuring a difference between the preliminary diagnosis prediction $y_{pre}$ and the patient-level label $\hat{y}$. The loss function can be any classification loss, such as softmax cross-entropy loss and focal loss.

The instance importance calculator 140 is configured and trained for calculating K instance importances corresponding to the K preliminary instance embeddings respectively. The K instance importances are denoted as a={$a_k$}$_{k=1}^K$, where $a_k$ is the instance importance corresponding to the $k^{th}$ 2D MRI slice in the 3D MRI scan. The $k^{th}$ instance importance $a_k$ indicates clinical significance of the $k^{th}$ slice towards the diagnosis on the 3D MRI scan. The $k^{th}$ instance importance $a_k$ may be given by:

$$\alpha_k = \sqrt{\frac{1}{C}\sum_{c=1}^{C}\left(s_k(c) - \frac{1}{C}\right)^2},$$

where $s_k(c)=\Sigma_{d=1}^{D}w(c,d)z_k(d)$ is the instance contribution by the $k^{th}$ instance embedding towards the $c^{th}$ category of predefined prostate diseases; wherein w(c,d) is the instance importance parameter obtained by the preliminary classifier, and $z_k$ is the $k^{th}$ instance embedding, C is the total number of categories of predefined prostate diseases, and D is the total number of categories of the dimension of input features for the preliminary classifier.

The IGraph layers 150 are configured and trained for: generating K improved instance embeddings from the K preliminary instance embeddings respectively by exploiting discriminative embeddings. The K improved instance embeddings are denoted as $\tilde{Z}$={$\tilde{z}_k$}$_{k=1}^K$, where $\tilde{z}_k$ is the improved instance embedding corresponding to the $k^{th}$ 2D MRI slice of the 3D MRI scan. In particular, the K improved instance embeddings $\tilde{Z}$ is generated by performing a plurality of graph convolutions on the plurality of preliminary instance embeddings Z by the plurality of IGraph layers in a sequential manner.

Figure 3:
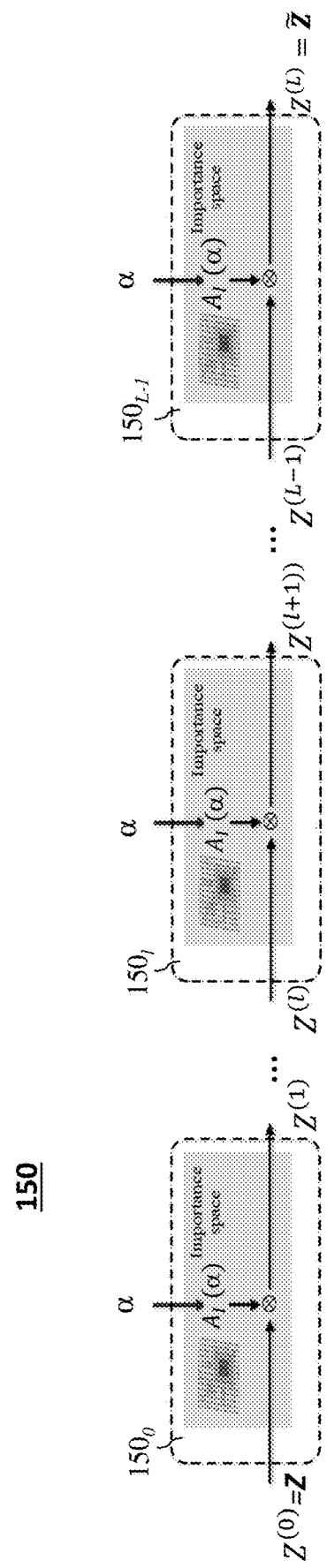
FIG. 3 shows more details of a plurality of IGraph layers according to one embodiment of the present invention.

FIG. 3 shows more details of the plurality of IGraph layers 150. As shown in FIG. 3, a $l^{th}$ IGraph layer $150_l$ is trained and configured to perform a $l^{th}$ graph convolution in an importance space to convert a $l^{th}$ input set instance embeddings $Z^{(l)}$ to a $l^{th}$ output set instance embeddings which is in turn a $(l+1)^{th}$ input set instance embeddings $Z^{(l+1)}$. The plurality of preliminary instance embeddings Z is fed to the first IGraph layer $150_0$ as an input set instance embeddings of the first IGraph layer $150_0$, that is $Z^{(0)}$=Z.

The plurality of improved instance embeddings $\tilde{Z}$ is generated by the last IGraph layer $150_{L-1}$ as an output set instance embeddings of the last IGraph layer $150_0$, that is $Z^{(L)}=\tilde{Z}$.

The $l^{th}$ graph convolution performed by the $l^{th}$ IGraph layer $150_l$ is defined as:

$$Z^{(l+1)}=\text{ReLU}(\widehat{A_l}Z^{(l)}W),$$

where $\widehat{A_l}$ is a degree normalized matrix of an adjacency matrix $A_l$, W is a set of learnable parameters to improve the input set instance embeddings $Z^{(l)}$, and ReLU is an adopted non-linear activation function.

The topology information of the input instance embedding $Z^{(l)}$ is utilized to formulate a graph for performing the graph convolution. Specifically, the instance embedding of each 2D slice may serve as a node in this graph, and the edge connections among these nodes are represented in the adjacency matrix $A_l$. The adjacency matrix $A_l$ is generated with mixtures of importance-based Gaussian and formulated by:

$$A_l=\Sigma_{k=1}^{K}a_kN([k,k],\sigma^2),$$

where $N([k,k],\sigma^2)$ is a peak value of a 2D Gaussian distribution corresponding to each 2D slice, which is centered at the $k^{th}$ diagonal entry of the adjacency matrix $A_l$ with variance $\sigma^2$, and each Gaussian component is weighted by a corresponding $k^{th}$ instance importance $a_k$.

Referring back to FIG. 2. The embedding aggregator 160 is configured and trained for aggregating the K improved instance embeddings $\tilde{Z}$ with the K instance importances $a=\{a_k\}_{k=1}^{K}$ to generate an improved bag embedding $z_I=\Sigma_{k=1}^{K}a_k\tilde{z}_k$.

The refined classifier 170 is configured and trained for processing the improved bag embedding $z_I$ to generate a refined diagnosis prediction y for predicting prostate health status of the patient. The refined diagnosis prediction y may be supervised with a loss function measuring a difference between the refined diagnosis prediction y and label ŷ, which can be any classification loss function, such as softmax cross-entropy loss function and focal loss function.

A cross-validation strategy may be adopted for the diagnostic assessment. In each split of cross-validation, the dataset is divided into training set, validation set and test set as 3:1:1. Specifically, the training set is used to optimize the GPD-Net, the validation set is used to adjust the hyperparameters of GPD-Net, and the test set is used to calculate the statistical metrics for performance evaluation.

The trained GDP-Net can be evaluated by various statistical metrics, including the accuracy, F1 score, sensitivity, specificity and area under receiver operating characteristic curve (AUC). Higher values of these metrics represent more accurate and reliable diagnosis predictions. For the diagnosis task with multiple categories (e.g., the prediction of Gleason score), binary metrics are first calculated for each category and then averaged in the macro manner. The performance is evaluated on test set using the model with the minimum validation loss.

By way of example, a 3D transaxial scans of one or several modal is adopted as the training dataset. A region of 192×192 is cropped to include the prostate as the input, and each MRI scan provides 20 slices. The 2D CNN extracts instance embeddings with 512 dimensions. The preliminary diagnosis stage is performed with the instance-wise average pooling and a fully-connected layer to generate a preliminary prediction. In the refined diagnosis stage, the output channels of two successive IGraph Layers are 512 and 256, respectively.

Figure 4:
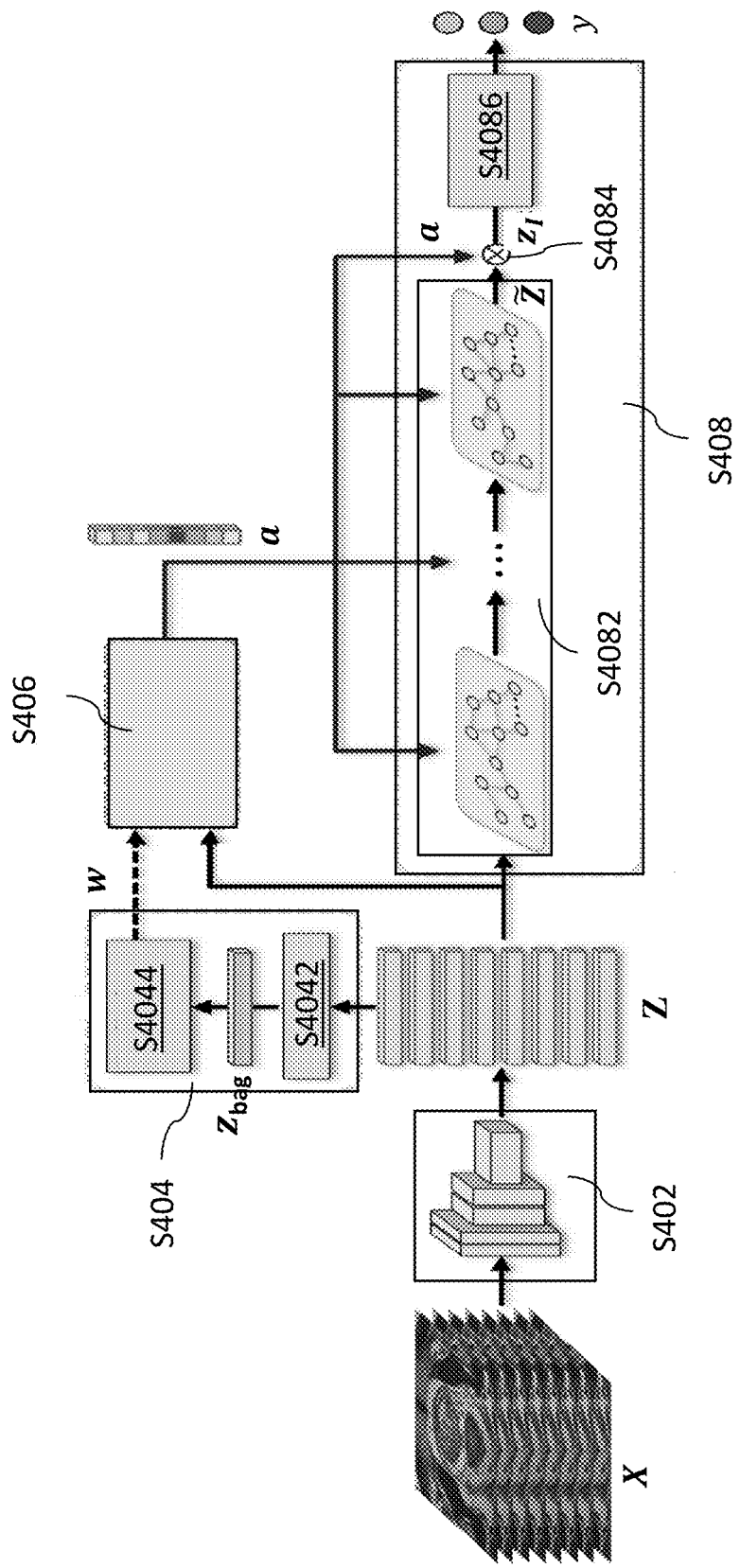
FIG. 4 shows an arrangement for using the GPD-Net to predict prostate health status of a patient according to one embodiment of the present invention.

FIG. 4 shows an arrangement for using the GPD-Net to predict prostate health status of a patient from a 3D MRI scan containing a plurality of 2D MRI slices X from that patient. As shown, the method may include the following stages: instance embedding extraction S402; preliminary diagnosis S404; instance importance calculation S406; refined diagnosis S408.

The instance embedding extraction stage S402 includes extracting, by a feature extractor, a plurality of preliminary instance embeddings Z corresponding to the plurality of 2D MRI slices X respectively; and The preliminary diagnosis stage S404 includes:

Step S4042: aggregating, by a pooling operator, the plurality of preliminary instance embeddings Z together to generate a preliminary bag embedding $z_{bag}$; and Step S4044: calculating, by a preliminary classifier, an instance importance parameter w based on the preliminary bag embedding $z_{bag}$.

The instance importance calculation stage S406 includes calculating, by an instance importance calculator, a plurality of instance importances a corresponding to the plurality of preliminary instance embeddings respectively based on the instance importance parameter w.

The refined diagnosis stage S408 includes:

Step S4082: generating, by a plurality of IGraph layers, a plurality of improved instance embeddings $\tilde{Z}$ by performing a plurality of graph convolutions on the plurality of preliminary instance embeddings Z in a sequential manner;

Step S4084: generating, by an embedding aggregator, an improved bag embedding $z_I$ by aggregating the plurality of improved instance embeddings $\tilde{Z}$ with the plurality of instance importances a; and Step S4086: processing, by a refined classifier, the improved bag embedding $z_I$ to generate a refined diagnosis prediction y for predicting prostate health status of the patient.

Figure 5:
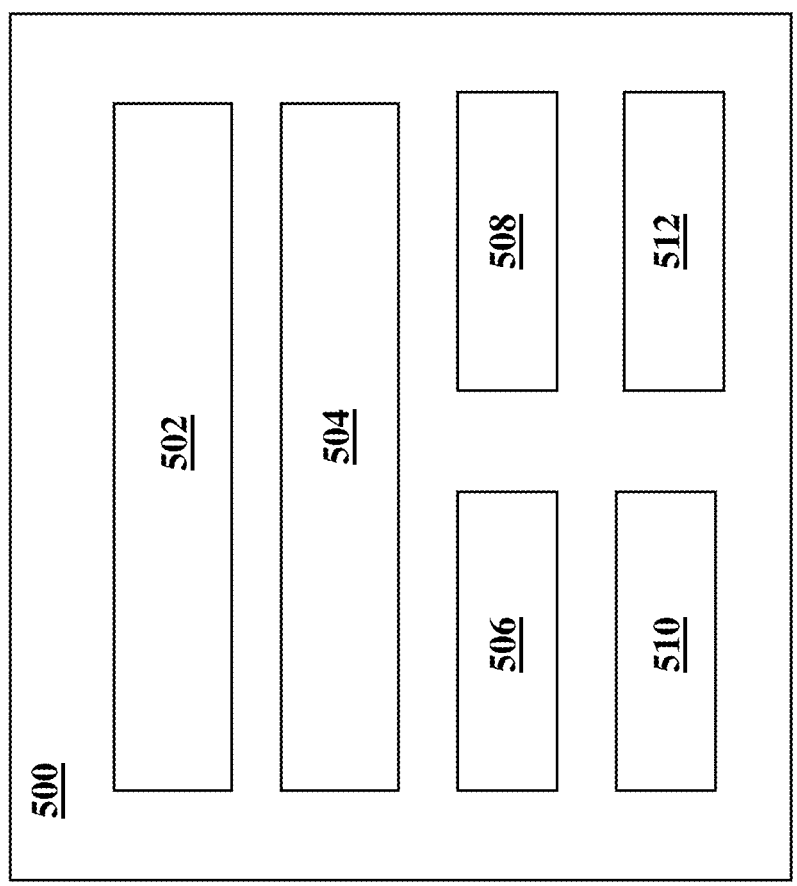
FIG. 5 is a block diagram of an exemplary system for training and deploying a GPD-Net for prostate diagnosis according to one embodiment of the present invention.

FIG. 5 is a block diagram of an exemplary system 500 for training and deploying a GPD-Net for prostate diagnosis according to one embodiment of the present invention. The system 500 may include at least one receiving module 502 configured for receiving or recording 3D MRI scans of a prostate of a patient.

The system 500 may further include a processor 504 which may be a CPU, an MCU, application specific integrated circuits (ASIC), field programmable gate arrays (FPGA) or any suitable programmable logic devices configured or programmed to be a processor for training and deploying the GPD-Net according to the teachings of the present disclosure.

The device 500 may further include a memory unit 506 which may include a volatile memory unit (such as RAM), a non-volatile unit (such as ROM, EPROM, EEPROM and flash memory) or both, or any type of media or devices suitable for storing instructions, codes, and/or data.

Preferably, the system 500 may further include one or more input devices 505 such as a keyboard, a mouse, a stylus, a microphone, a tactile input device (e.g., touch sensitive screen) and/or a video input device (e.g., camera). The system 500 may further include one or more output devices 510 such as one or more displays, speakers and/or disk drives. The displays may be a liquid crystal display, a light emitting display or any other suitable display that may or may not be touch sensitive.

The system 500 may also preferably include a communication module 512 for establishing one or more communication links (not shown) with one or more other computing devices such as a server, personal computers, terminals, wireless or handheld computing devices. The communication module 512 may be a modem, a Network Interface Card (NIC), an integrated network interface, a radio frequency transceiver, an optical port, an infrared port, a USB connection, or other interfaces. The communication links may be wired or wireless for communicating commands, instructions, information and/or data.

Preferably, the receiving module 502, the processing unit 504, the memory unit 506, and optionally the input devices 505, the output devices 510, the communication module 512 are connected with each other through a bus, a Peripheral Component Interconnect (PCI) such as PCI Express, a Universal Serial Bus (USB), and/or an optical bus structure. In one embodiment, some of these components may be connected through a network such as the Internet or a cloud computing network. A person skilled in the art would appreciate that the system 500 shown in FIG. 5 is merely exemplary, and that different systems 500 may have different configurations and still be applicable in the invention.

The foregoing description of the present invention has been provided for the purposes of illustration and description. It is not intended to be exhaustive or to limit the invention to the precise forms disclosed. Many modifications and variations will be apparent to the practitioner skilled in the art.

The apparatuses and the methods in accordance to embodiments disclosed herein may be implemented using computing devices, computer processors, or electronic circuitries and other programmable logic devices configured or programmed according to the teachings of the present disclosure. Computer instructions or software codes running in the computing devices, computer processors, or programmable logic devices can readily be prepared by practitioners skilled in the software or electronic art based on the teachings of the present disclosure.

All or portions of the methods in accordance to the embodiments may be executed in one or more computing devices including server computers, personal computers, laptop computers, mobile computing devices such as smartphones and tablet computers.

The embodiments were chosen and described in order to best explain the principles of the invention and its practical application, thereby enabling others skilled in the art to understand the invention for various embodiments and with various modifications that are suited to the particular use contemplated.

What is claimed is:

1. A graph-based prostate diagnosis network for predicting a prostate health status of a patient from a 3D magnetic resonance imaging (MRI) scan containing a plurality of 2D MRI slices, the graph-based prostate diagnosis network comprising:
a feature extractor configured to extract a plurality of preliminary instance embeddings Z corresponding to the plurality 2D MRI slices X respectively;
a pooling operator configured to aggregate the plurality of preliminary instance embeddings Z together to generate a preliminary bag embedding;
a preliminary classifier configured to calculate an instance importance parameter w based on the preliminary bag embedding $z_{bag}$;
an instance importance calculator configured to calculate a plurality of instance importances a corresponding to the plurality of preliminary instance embeddings respectively based on the instance importance parameter w; and
a plurality of importance-guided graph (IGraph) layers configured to generate a plurality of improved instance embeddings $\tilde{Z}$ by performing a plurality of graph convolutions on the plurality of preliminary instance embeddings Z in a sequential manner;
an embedding aggregator configured to generate an improved bag embedding $z_I$ by aggregating the plurality of improved instance embeddings $\tilde{Z}$ with the plurality of instance importances a; and
a refined classifier configured to process the improved bag embedding $z_I$ to generate a refined diagnosis prediction y for predicting prostate health status of the patient.

2. The graph-based prostate diagnosis network according to claim 1, wherein
a $l^{th}$ graph convolution of the plurality of graph convolutions is performed by a $l^{th}$ IGraph layer of the plurality of IGraph layers and defined as:

$$Z^{(l+1)} = \text{ReLU}(\widehat{A_I} Z^{(l)} W),$$

where $Z^{(l)}$ represents an input set instance embeddings of the $l^{th}$ IGraph layer, $Z^{(l+1)}$ represents an output set instance embeddings of the $l^{th}$ IGraph layer, $\widehat{A_I}$ is a degree normalized matrix of an adjacency matrix $A_I$, W is a set of learnable parameters to improve the input set instance embeddings $Z^{(l)}$, and ReLU is an adopted non-linear activation function.

3. The graph-based prostate diagnosis network according to claim 2, wherein
the plurality of preliminary instance embeddings Z is an input set instance embeddings of a first IGraph layer of the plurality of IGraph layers; and
the plurality of improved instance embeddings $\tilde{Z}$ is an output set instance embeddings of a last IGraph layer of the plurality of IGraph layers.

4. A method for training a graph-based prostate diagnosis network including a feature extractor, a pooling operator, a preliminary classifier, an instance importance calculator, a plurality of importance-guided graph (IGraph) layers, an embedding aggregator and a refined classifier, the method comprising:
preparing a training dataset of 3D magnetic resonance imaging (MRI) scans, each having a patient-level label $\hat{y}$ and containing a plurality of 2D MRI slices;
for each of the 3D MRI scans:
feeding the 3D MRI scan to the feature extractor and training the feature extractor, to extract a plurality of preliminary instance embeddings Z corresponding to a plurality of 2D MRI slices of the fed 3D MRI scan respectively;
feeding the plurality of preliminary instance embeddings Z to the pooling operator and training the pooling operator to aggregate the plurality of preliminary instance embeddings Z together to generate a preliminary bag embedding $z_{bag}$;
feeding the preliminary bag embedding $z_{bag}$ to the preliminary classifier, and training the preliminary classifier to:
process the preliminary bag embedding $z_{bag}$ to generate a preliminary diagnosis prediction $y_{pre}$;
calculate an instance importance parameter w based on the preliminary bag embedding $z_{bag}$; and
adjust the instance importance parameter w under supervision with a loss function measuring a difference between the preliminary diagnosis prediction and a patient-level label corresponding to the fed 3D MRI scan;
feeding the instance importance parameter w and the plurality of preliminary instance embeddings Z to the instance importance calculator and training the instance importance calculator to calculate a plurality of instance importances a corresponding to the plurality of preliminary instance embeddings respectively based on the instance importance parameter w;

feeding the plurality of preliminary instance embeddings Z to the plurality of IGraph layers and training the plurality of IGraph layers to generate a plurality of improved instance embeddings $\tilde{Z}$ by performing a plurality of graph convolutions on the plurality of preliminary instance embeddings Z in a sequential manner;

feeding the plurality of improved instance embeddings $\tilde{Z}$ and the plurality of instance importances a to the embedding aggregator and training the embedding aggregator to generate an improved bag embedding $z_I$ by aggregating the plurality of improved instance embeddings $\tilde{Z}$ with the plurality of instance importances a;

feeding the improved bag embedding $z_I$ to the refined classifier and training the refined classifier to process the improved bag embedding $z_I$ to generate a refined diagnosis prediction y under supervision with a loss function measuring a difference between the refined diagnosis prediction and the patient-level label corresponding to the fed 3D MRI scan.

5. The method according to claim 4, the training dataset of 3D MRI scans include one or more modal of multiparametric MRI data.

6. The method according to claim 5, the one or more modal of multiparametric MRI data include diffusion weighted images.

7. The method according to claim 5, the one or more modal of multiparametric MRI data include apparent diffusion coefficient maps.

8. The method according to claim 5, the one or more modal of multiparametric MRI data include Ktrans (a measure of capillary permeability obtained using dynamic contrast-enhanced (DCE) magnetic resonance perfusion).

9. The method according to claim 5, the one or more modal of multiparametric MRI data include T2 (transverse relation time) weighted images.

10. The method according to claim 4, wherein the patient-level label is an existence of clinically significant biomarkers.

11. The method according to claim 4, wherein the patient-level label is a Gleason grading score.

12. The method according to claim 4, wherein the loss function measuring the difference between the preliminary diagnosis prediction and the patient-level label corresponding to the fed 3D MRI scan is a softmax cross-entropy loss function.

13. The method according to claim 4, wherein the loss function measuring the difference between the refined diagnosis prediction and the patient-level label corresponding to the fed 3D MRI scan is a softmax cross-entropy loss function.

14. The method according to claim 4, wherein the loss function measuring the difference between the preliminary diagnosis prediction and the patient-level label corresponding to the fed 3D MRI scan is a focal loss function.

15. The method according to claim 4, wherein the loss function measuring the difference between the refined diagnosis prediction and the patient-level label corresponding to the fed 3D MRI scan is a focal loss function.

16. A method for using a graph-based prostate diagnosis network to predict a prostate health status of a patient from a 3D magnetic resonance imaging (MRI) scan containing a plurality of 2D MRI slices, the method comprising:

an instance embedding extraction stage including extracting, by a feature extractor, a plurality of preliminary instance embeddings Z corresponding to the plurality of 2D MRI slices X respectively;

a preliminary diagnosis stage including:
aggregating, by a pooling operator, the plurality of preliminary instance embeddings Z together to generate a preliminary bag embedding $z_{bag}$; and
calculating, by a preliminary classifier, an instance importance parameter w based on the preliminary bag embedding $z_{bag}$;

an instance importance calculation stage including calculating, by an instance importance calculator, a plurality of instance importances a corresponding to the plurality of preliminary instance embeddings respectively based on the instance importance parameter w; and a refined diagnosis stage including:
generating, by a plurality of importance-guided graph (IGraph) layers, a plurality of improved instance embeddings $\tilde{Z}$ by performing a plurality of graph convolutions on the plurality of preliminary instance embeddings Z in a sequential manner;
generating, by an embedding aggregator, an improved bag embedding $z_I$ by aggregating the plurality of improved instance embeddings $\tilde{Z}$ with the plurality of instance importances a; and
processing, by a refined classifier, the improved bag embedding $z_I$ to generate a refined diagnosis prediction y for predicting prostate health status of the patient.

17. The method according to claim 16, wherein a $l^{th}$ graph convolution of the plurality of graph convolutions is performed by a $l^{th}$ IGraph layer of the plurality of IGraph layers and defined as:

$$Z^{(l+1)} = \text{ReLU}(\widehat{A_l} Z^{(l)} W),$$

where $Z^{(l)}$ represents an input set instance embeddings of the $l^{th}$ IGraph layer, $Z^{(l+1)}$ represents an output set instance embeddings of the $l^{th}$ IGraph layer, $\widehat{A_l}$ is a degree normalized matrix of an adjacency matrix $A_l$, W is a set of learnable parameters to improve the input set instance embeddings $Z^{(l)}$, and ReLU is an adopted non-linear activation function.

18. The method according to claim 17, wherein
the plurality of preliminary instance embeddings Z is an input set instance embeddings of a first IGraph layer of the plurality of IGraph layers; and
the plurality of improved instance embeddings $\tilde{Z}$ is an output set instance embeddings of a last IGraph layer of the plurality of IGraph layers.

* * * * *